United States Patent
Högerle et al.

(10) Patent No.: US 12,035,876 B2
(45) Date of Patent: Jul. 16, 2024

(54) INTEGRATED POWER UNIT (IPU)

(71) Applicant: Aesculap AG, Tuttlingen (DE)

(72) Inventors: Roland-Alois Högerle, Tuttlingen (DE); Uwe Mattes, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 540 days.

(21) Appl. No.: 17/415,785

(22) PCT Filed: Dec. 20, 2019

(86) PCT No.: PCT/EP2019/086567
§ 371 (c)(1),
(2) Date: Jun. 18, 2021

(87) PCT Pub. No.: WO2020/127901
PCT Pub. Date: Jun. 25, 2020

(65) Prior Publication Data
US 2022/0071639 A1    Mar. 10, 2022

(30) Foreign Application Priority Data

Dec. 21, 2018   (DE) .................... 10 2018 133 504.0

(51) Int. Cl.
*A61B 17/16*    (2006.01)
*A61B 90/53*    (2016.01)
*A61B 17/00*    (2006.01)

(52) U.S. Cl.
CPC .......... *A61B 17/1628* (2013.01); *A61B 90/53* (2016.02); *A61B 2017/00017* (2013.01); *A61B 2017/00734* (2013.01)

(58) Field of Classification Search
CPC ............... A61B 17/1628; A61B 90/53; A61B 2017/00017; A61B 2017/00734;
(Continued)

(56) References Cited

U.S. PATENT DOCUMENTS 6,633,278 B1    10/2003   Hoegener et al.
9,559,624 B2    1/2017    Philipp
(Continued)

FOREIGN PATENT DOCUMENTS

CN    105982702 A    10/2016
CN    107106201 A    8/2017
(Continued)

OTHER PUBLICATIONS

Written Opinion received in International Application No. PCT/EP2019/086567 dated Mar. 26, 2020, with translation, 17 pages.
(Continued)

*Primary Examiner* — Michael J Brown
(74) *Attorney, Agent, or Firm* — Christopher A. Rothe; Culhane PLLC

(57) ABSTRACT

A power supply unit for a surgical instrument operated by an electric motor includes a battery-receiving housing separate and spaced apart from the surgical instrument. A fastening means or retainer fastens or retains the power supply unit to a body part of an operator. At least one power supply unit supplies power to at least one motor system. A control and monitoring device performs and/or monitors at least one function. A cable connection connects a cable for electrically coupling the power supply unit to a surgical instrument for operating the motor system thereof and/or for transmitting data and/or operating parameters.

11 Claims, 1 Drawing Sheet

(58) Field of Classification Search
CPC .......... A61B 2017/00221; A61B 2017/00442; A61B 2017/00199; A61B 2017/00973; A61B 2090/0807
USPC ........................................................ 700/297
See application file for complete search history.

(56) References Cited

U.S. PATENT DOCUMENTS

| | | | |
|---|---|---|---|
| 9,619,618 B2 | 4/2017 | Ingmanson | |
| 2002/0086264 A1 | 7/2002 | Okawa et al. | |
| 2004/0035242 A1 | 2/2004 | Peterson et al. | |
| 2006/0047200 A1 | 3/2006 | Miyazawa | |
| 2007/0085496 A1* | 4/2007 | Philipp | A61B 17/151 |
| | | | 318/139 |
| 2009/0205937 A1 | 8/2009 | Kuehner et al. | |
| 2010/0241151 A1 | 9/2010 | Rickard | |
| 2012/0011293 A1 | 1/2012 | Cheng et al. | |
| 2016/0073855 A1 | 3/2016 | Farr et al. | |
| 2016/0174018 A1 | 6/2016 | Schönewerk | |
| 2016/0375273 A1 | 12/2016 | Hirai et al. | |
| 2017/0007219 A1 | 1/2017 | Bucina et al. | |
| 2017/0360466 A1 | 12/2017 | Brown et al. | |
| 2018/0043146 A1* | 2/2018 | Vescovi | A61M 37/0076 |
| 2018/0055591 A1 | 3/2018 | Bonny et al. | |
| 2018/0070943 A1 | 3/2018 | Malinouskas et al. | |
| 2018/0341400 A1 | 11/2018 | Kim et al. | |
| 2020/0253628 A1 | 8/2020 | Brown et al. | |

FOREIGN PATENT DOCUMENTS

| | | |
|---|---|---|
| DE | 102005029458 A1 | 12/2006 |
| DE | 102013114918 A1 | 7/2015 |
| EP | 1326565 B1 | 7/2003 |
| EP | 1567063 B1 | 8/2005 |
| EP | 1698373 A1 | 9/2006 |
| EP | 3070627 A1 | 9/2016 |
| EP | 3032513 B1 | 8/2017 |
| JP | 2001142003 A | 5/2001 |
| JP | 2002143183 A | 5/2002 |
| JP | 2006068220 A | 3/2006 |
| JP | 2007029451 A | 2/2007 |
| JP | 2008546503 A | 12/2008 |
| JP | 2011206596 A | 10/2011 |
| JP | 2011218164 A | 11/2011 |
| JP | 2013536613 A | 9/2013 |
| JP | 2017018598 A | 1/2017 |
| WO | 0121056 A2 | 3/2001 |
| WO | 2008092042 A2 | 7/2008 |
| WO | 2016100522 A1 | 6/2016 |
| WO | 2016161322 A1 | 10/2016 |
| WO | 2017189606 A1 | 11/2017 |

OTHER PUBLICATIONS

Search Report received in International Application No. PCT/EP2019/086567 dated Mar. 26, 2020, with translation, 7 pages.
Search Report received in German Application No. 10 2018 135 504.0 dated Nov. 5, 2019, with translation, 19 pages.
Search Report received in German Application No. 10 2019 101 308.9 dated Sep. 13, 2019, with translation, 19 pages.
Search Report received in International Application No. PCT/EP2020/0050807 dated Mar. 30, 2020, with translation, 5 pages.
Written Opinion received in International Application No. PCT/EP2020/0050807 dated Mar. 30, 2020, with translation, 11 pages.
Office Action received in Japanese Application No. 2021-535979 dated Jul. 21, 2023, with translation, 32 pages.
Office Action received in Japanese Application No. 2021-541177 dated Jul. 20, 2023, with translation, 7 pages.
Office Action received in Japanese Application No. 2021-535979 dated Feb. 20, 2024, with translation, 10 pages.
Office Action received in Chinese Application No. 202080008085.1 dated Mar. 1, 2024, with translation, 14 pages.
Office Action received in Japanese Application No. 2021-541177 dated Mar. 5, 2024, with translation, 8 pages.

* cited by examiner

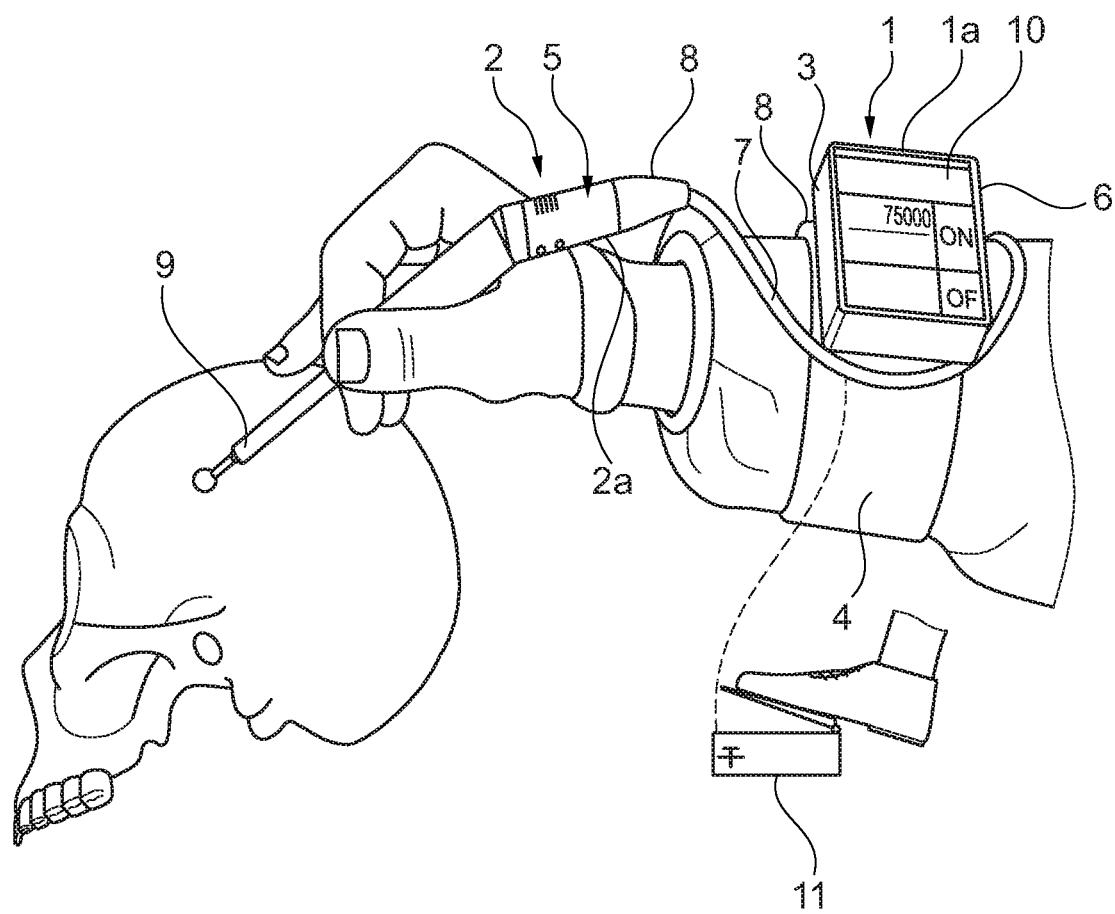

INTEGRATED POWER UNIT (IPU)

CROSS-REFERENCE TO RELATED APPLICATION(S)

This application is the United States national phase entry of International Application No. PCT/EP2019/086567, filed Dec. 20, 2019, and claims the benefit of priority of German Application No. 10 2018 133 504.0, filed Dec. 21, 2018. The contents of International Application No. PCT/EP2019/086567 and German Application No. 10 2018 133 504.0 are incorporated by reference herein in their entireties.

FIELD

The present disclosure relates to a power supply unit for an or of an electromotively-operated surgical instrument, preferably of the minimally invasive type, and to a surgical treatment system.

BACKGROUND

Systems of microsurgery should be able to be operated wirelessly, comparable to macrosurgery, so that the connection from the sterile area, such as the operating field, to the non-sterile area is eliminated. Such connections are currently cables/lines, which form a bridge between the sterile area and the non-sterile area and, in the worst case, run transversely through the operating room, posing a risk of falling for hospital personnel. This poses a considerable risk, such as a defect caused by the cable being rolled over by a trolley and/or hospital bed or the like. Likewise, the use of such lines can lead to decoupling/disconnecting during operation. Another disadvantage of these cables is the necessary length of the respective cables.

All known battery solutions currently do not meet the requirements of microsurgery, since the combination of the surgical instrument with the motor system connected to it or installed in it to form a drive-integral handpiece and an additional battery integrated into the handpiece neither meets the desired/required manufactured size nor the weight requirements of the handpiece. Ergonomics and good handling also cannot be adequately achieved with an power storage unit integrated in the handpiece. If the power supply unit as well as the necessary motor electronics, the operating elements and also the display for displaying certain motor and/or operating parameters are permanently connected to or integrated with the handpiece, this is inevitably too heavy, too large and too unwieldy. Thus, a major disadvantage of the products/systems already on the market is that difficile microsurgical work cannot be performed as usual.

In the prior art, a single-cell power supply unit for a motorized surgical instrument (or system) comprising a single-cell power supply housing is already known from WO 2016/161322 A1. A high-temperature battery cell is mechanically held and disposed in a center of the single-cell power supply housing. An electrical connector having a plurality of connector pins is configured to be coupled to a mating electrical connector of a tool part having a motor.

However, a fundamental disadvantage of this prior art is that when using an (integrally formed) single-cell power supply unit for a motorized surgical instrument (or system), the manufactured size of the motor-operated surgical instrument (or system) is unacceptable and there is insufficient performance and reliability.

SUMMARY

The present invention is therefore based on the object of providing a power supply unit for an or of an electromotively-driven surgical instrument and a surgical treatment system, which avoids or at least improves the disadvantages of the prior art.

The core of the present invention substantially is to provide the power supply (unit) of or for an electromotively-driven surgical instrument separately and spatially spaced therefrom but still within a sterile area and preferably as close as possible to the surgical instrument. In other words, the present invention provides in principle for the electric motor/motor system of a surgical instrument to be arranged/installed in/on a handpiece of the instrument in accordance with the state of the art, and to integrate/arrange its control device, power supply and, if applicable, display for (visual) representation, for example, motor characteristics and/or operating parameters in/on a component which is separate from and spatially spaced apart from the surgical instrument/its handle and which is preferably designed to be carried along in a mobile manner on the body of an instrument operator (surgeon who is currently holding the instrument in his hand), preferably in such a way that, during operation of the instrument, its control can be actuated manually and/or the display can be read visually by the instrument operator.

In this way, the (mass) weight as well as the manufactured size of the surgical instrument can be kept at a low level, making it particularly usable in microsurgery, and at the same time a sterile barrier is not broken by at least one cable, in particular a power supply cable or the like, which has to be connected to an external power supply, for example.

The object of the invention is specifically solved in that a (stand-alone/power grid-independent) power supply unit is provided with a battery-receiving housing which is separate from and spatially spaced apart from the surgical instrument and which is designed or provided with a fastening means or a retainer—adapted for temporary fastening or retaining of the power supply unit to a body part of an instrument operator. Furthermore, the power supply unit is equipped with at least one power storage unit, which is designed for a power supply of at least one motor system, in particular an electric motor, of a surgical instrument connected or connectable thereto. In addition, the power supply unit has an (internal/own) control and monitoring device preferably (at least partially) on an outside of the battery-receiving housing or with actuation means on the outside of the housing, wherein the control and monitoring device is designed to perform and/or monitor at least one of the following functions:

the control and monitoring unit can monitor/display a state of charge of an power storage unit, and/or
switch on/off a power supply to a surgical instrument connected thereto, and/or
receive and/or send data from the power supply unit to an additional external instrument actuation unit, preferably a radio foot control or hand control, and/or
output and/or receive operating parameters and operating signals to/from a/the surgical instrument connected thereto, preferably with respect to its motor system, and/or
save data and/or operating parameters.

Furthermore, the power supply unit is preferably designed/provided with a (single) cable/wire harness and/or a cable connection for connecting the cable/wire harness for electrically coupling the power supply unit with a/the surgical instrument for operating its electric motor and/or for transmitting the data and/or operating parameters.

In other words, the entire supply of the motor system as well as the communication between the power supply unit and the motor-operated surgical instrument takes place via exactly one cable/wire harness. Thus, the solution according to the invention of the present object realizes that this cable does not form a bridge from the non-sterile area to the sterile area. Furthermore, by outsourcing the power supply and control from the handle of the surgical instrument (while retaining the mobility of the power supply and control unit), the surgical instrument with integrated motor system can be made smaller and more manageable than in the prior art already known, and preferably the loading capacity of the power supply unit can be increased. Since both the surgical instrument and the power supply unit are located in the sterile area, no extra preparation is necessary and the entire set-up can be placed in the sterile area, in particular also on the patient.

It is preferred if the power supply unit is designed with a battery or an accumulator. More preferred is the use of an accumulator, which is rechargeable and thus both less costly and more environmentally friendly than a battery. A further advantage of such an accumulator or battery may be that it (just like the control and monitoring device) can be designed to be removable from the power supply unit or from its receiving housing, so that the housing of the power supply unit can be sterilized, for example, without any risk of damage to the storage unit and control system. Such an embodiment also allows the power storage unit to be replaced or recharged in the absence of a patient, i.e. in an offline operating mode.

More specifically, it is intended to provide a stand-alone power supply unit with a power storage, which has a battery-receiving housing that is preferably attached to the wrist or forearm of an operator, in particular a surgeon, and is thus connected to the surgical instrument with a relatively short cable.

It is further preferred if the external instrument actuation unit is designed as a hand control and/or as a radio foot control, which preferably communicates wirelessly with the power supply unit or the control and monitoring device incorporated therein for operating an application part respectively inserted into the handpiece of the instrument. Application part is understood to mean a tool that is inserted into the handle of a surgical instrument with the motor system integrated therein. In other words, application parts/handpieces (inserted tools) can be operated either by hand control or alternatively by foot control (via the control and monitoring device). Ideally, all the technical advantages of the previously known cable-operated or mains-connected systems can thus be utilized. Such technical advantages are, for example, an (automatic) application part/tool recognition, a data acquisition system and/or an assignment of a total operating time to a tool used.

It is further preferred if the power supply unit has a display which serves for operating the power supply unit and/or for displaying information. Since the power supply unit is adapted to be fastened/fixed preferably to the wrist or forearm of an operator, it is advantageous to form/arrange the display on the upper side (the side facing away from the lower arm) of the power supply unit at its battery-receiving housing. By fixing it especially on the wrist or forearm of an operator of the surgical instrument, it is easy for the operator to keep the display in view, preferably according to a 'control watch', when holding the instrument in (the same) hand. Furthermore, the operation of such a control watch is facilitated for the operator by its arrangement in his/her immediate vicinity and in the sterile area, whereby additional separate (possibly non-sterile) components, such as a separate/additional control device, are not required. This has the advantage that space in the operating room can be saved and all cables running across the operating room can be dispensed with in order to reduce tripping hazards and the risk of injury.

Furthermore, it is preferred if the display shows the state of charge of the power storage and has buttons for switching the power supply on and off. This makes it easier for the operator to operate and also monitor the control and monitoring unit of the power supply unit.

It is further preferred if the fastening means of the power supply unit is designed as a cuff, preferably with a hook and loop fastener. It is advantageous if the fastening means of the power supply unit is designed in such a way that it can be quickly and easily attached to the user/operator, i.e. his/her wrist or forearm, and can also be quickly and easily removed again by the user/operator.

It is further preferred if the battery-receiving housing is designed to be fluid-tight, preferably such that it protects against splash water. This ensures a longer service life for the power storage unit integrated in the power supply unit and for existing control components. Furthermore, individual components of the power supply unit can be replaced more easily, thus reducing costs and material waste.

Furthermore, it is preferred if the cable between the power supply unit and the surgical instrument is just long enough to connect the motor system within a/the handle or handpiece of a surgical instrument to the power supply unit at the wrist/forearm of the surgeon holding the instrument. This short cable can reduce technical problems/interferences, such as those in the area of EMC and/or signal transmission.

It is also preferred if both the power supply unit and the motor system and the application part (tool) or the surgical instrument can be set down in the sterile area. This means, for example, that the entire system can also be placed on the patient.

Furthermore, the present invention relates to a surgical treatment system with:
a surgical instrument operated by an electric motor, the (integrated) motor system of which, in particular an electric motor designed for operation via a (direct current) power storage unit, is accommodated in a handpiece/handle of the instrument, wherein at the proximal end or end region of which a cable connection or a cable for the power supply of at least the motor system and/or for the transmission of data and/or operating parameters is formed or arranged, and
with a power supply unit having the features according to one of the preceding aspects.

Thus, the solution of the present invention meets the requirements of surgery, in particular microsurgery, such as minimum manufactured size, minimum weight, good ergonomics and good handling of the surgical instrument. The problems stated at the beginning concerning the power supply, the motor electronics, the control elements and a display, which is firmly connected to the application part, are eliminated or at least reduced by the present invention.

BRIEF DESCRIPTION OF THE DRAWING FIGURE

The FIGURE is a diagram illustrating the surgical treatment system according to the present disclosure.

DETAILED DESCRIPTION

Hereinafter, a preferred embodiment of the present disclosure is described in more detail based on the accompanying FIGURE. The FIGURE is merely schematic in nature and is provided for the purpose of understanding the invention. Identical elements are designated by the same reference signs.

The FIGURE is a diagram illustrating the surgical treatment system according to the present disclosure. The FIGURE shows a power supply unit 1 for an electromotively-operated surgical instrument 2. The surgical instrument 2 is formed separately from the power supply unit 1 and is spatially spaced therefrom. It has a preferably sleeve-shaped handle/handpiece 2a, in which a motor system (electric motor) 5 is accommodated, which can be actuated via actuation elements on the handle (not shown further). At the distal end/end portion of the handle 2a there is usually a receiving device for a tool (application part) 9, which is driven e.g. rotationally by the motor system 5. At the proximal end/end portion of the handle 2a, a connection 8 for a cable 7 (wire harness) is arranged/formed or the cable 7 (wire harness) is firmly mounted on the handle 2a. In this respect, the present surgical instrument 2 corresponds to the instruments of the present applicant already known from the prior art, so that reference can be made to these instruments at this point.

The separate power supply unit 1 has a receiving housing 3 for a power storage unit 1a (hereinafter simply referred to as battery-receiving housing), which has a fastening means/retainer 4 or to which a fastening means/retainer 4 is mounted, which is adapted for temporary fastening/retaining of the power supply unit 1 in particular to a body part (wrist/forearm) of an operator of the surgical instrument 2. Furthermore, the power supply unit 1 has the power storage unit 1a (inside the housing 3 and therefore not further shown), which is preferably an accumulator or a battery and which is adapted for the power supply of at least the motor system 5 of a surgical instrument 2 straightly connected thereto. Furthermore, the power supply unit 1 has a control and monitoring device 6, which is preferably arranged at least partially on an outer side of the battery-receiving housing 3 (or whose actuation means such as buttons and the like are arranged on an outer side of the battery-receiving housing 3).

The power supply unit 1 is coupled/couplable with the cable 7 via a further cable connection 8 formed/arranged in/on the battery-receiving housing 3. The cable 7 and the cable connection 8 serve to electrically couple the power supply unit 1 to the surgical instrument 2 for operating its motor system 5 and/or for transmitting the data and/or operating parameters, in particular from the surgical instrument 2 to the power supply unit 1.

Furthermore, it is readily apparent from the FIGURE that the tool/application part 9 is preferably a shank tool which is suitable for (manual) microsurgical use. I.e., the surgical instrument 2 is provided to be guided during operation, in particular manually, on the tool handle 5, wherein the power supply unit 1 coupled to the instrument 2 via cable 7, including the control and monitoring device 6, power storage unit 1a and display 10 installed therein, is fixed to the wrist or forearm of the guide hand via the fastening means 4, preferably a cuff or strap. Thus, the surgical instrument 2 can be built to be light and thus can be easily maneuvered, while at the same time the power supply as well as control of the instrument 2 is ensured and finally the display 10 can be easily read. For this purpose, the power supply unit 1 has the display 10 on its upper side (upper side of the battery-receiving housing 3) preferably in the form of a digital display (touch screen). The display 10 has integrated therein a state of charge of the energy-storage, an on/off switch for the power supply and an adjustment possibility, which is represented with plus or minus, for the regulation of the power to be supplied.

Furthermore, the FIGURE shows the attachment of the power supply unit 1 to the operator's forearm via the fastening means 4. The fastening means 4 in this case is preferably a cuff, which can further preferably be applied to the forearm like a watch or by means of a Velcro fastener.

Furthermore, it can be seen in the FIGURE that the cable 7 from the power supply unit 1 to the motor system 5 of the surgical instrument 2 is just short enough to electrically connect the power supply unit 1 to the motor-operated surgical instrument 2 without disturbing or hindering the operator in his/her use of the surgical instrument 2. Finally, an optional radio foot control 11 is shown symbolically in the FIGURE, which is in radio contact with the power supply unit 1 in order to regulate the speed of the motor system in the surgical instrument 2, for example (as an alternative or in addition to the operating elements in the handle 2a).

Finally, it should be noted that although the embodiment shown relates to a manual surgical instrument, the handpiece can, for example, be replaced/supplemented by an assembly interface (quasi as an adapter) which is configured to be mechanically mounted on a robot arm. In this case, the power supply unit can be temporarily fixed to the robot arm.

The invention claimed is:

1. A power supply unit for an electromotively-operated surgical instrument, the power supply unit designed or provided as a separate component spaced from the surgical instrument and comprising:
   a fastening means or retainer adapted for temporary fastening or retaining of the power supply unit to a body part of an operator of the surgical instrument;
   at least one power storage unit designed for supplying power to at least one motor system of the surgical instrument, the at least one power storage unit accommodated in a receiving housing of the power supply unit;
   a control and monitoring device within the receiving housing, the control and monitoring device configured to perform and/or monitor at least one of the following functions:
      monitoring and/or displaying a state of charge of the at least one power storage unit,
      switching on/off a power supply to the surgical instrument,
      receiving and/or sending data to an external instrument actuation unit,
      and
      storing data and/or operating parameters; and
   a cable and a cable connection for connecting the cable for electrically coupling the power supply unit to the surgical instrument for operating the at least one motor system and/or for transmitting data and/or operating parameters,
   wherein the control and monitoring device is additionally configured to output and receive operating parameters and operating signals to and from the surgical instrument.

2. The power supply unit according to claim 1, wherein the external instrument actuation unit is a manual control and/or a radio foot control and which communicates wirelessly with an application part.

3. The power supply unit according to claim 1, wherein the power supply unit comprises a display that operates the power supply unit and displays information.

4. The power supply unit according to claim 3, wherein the display indicates the state of charge of the at least one power storage unit and has buttons for switching the power supply on and off.

5. The power supply unit according to claim 1, wherein the fastening means or retainer comprises a cuff.

6. The power supply unit according to claim 1, wherein the receiving housing is fluid-tight.

7. The power supply unit according to claim 1, wherein the cable is formed just long enough to connect the at least one motor system to the power supply unit at a wrist or forearm of the operator.

8. A surgical treatment system comprising:
the power supply unit according to claim 1; and
an electromotively-operated surgical instrument with a motor system,
the motor system configured for operation by a power storage unit and accommodated in a handpiece of the surgical instrument, the surgical instrument comprising a cable connection at a proximal end or end region of the handpiece, the cable connection configured for supplying power to the motor system and/or for transmitting data and/or operating parameters.

9. The surgical treatment system according to claim 8, wherein the motor system is configured to be operated with direct current.

10. The power supply unit according to claim 1, further comprising a battery or an accumulator, the battery or the accumulator being removable from the receiving housing so that the receiving housing is sterilizable without risk of damage to the at least one power storage unit and the control and monitoring device.

11. A power supply unit for an electromotively-operated surgical instrument, the power supply unit designed or provided as a separate component spaced from the surgical instrument and comprising:
a fastener or retainer adapted for temporary fastening or retaining of the power supply unit to a body part of an operator of the surgical instrument;
at least one power storage unit designed for supplying power to at least one motor system of the surgical instrument, the at least one power storage unit accommodated in a receiving housing of the power supply unit;
a control and monitoring device within the receiving housing, the control and monitoring device comprising at least one of:
a display or touchscreen for monitoring and/or displaying a state of charge of the at least one power storage unit,
a switch for switching on/off a power supply to the surgical instrument,
an interface for receiving and/or sending data to an external instrument actuation unit,
and
a storage medium for storing data and/or operating parameters; and
a cable and a cable connection for connecting the cable for electrically coupling the power supply unit to the surgical instrument for operating the at least one motor system and for transmitting data and/or operating parameters,
wherein the control and monitoring device additionally comprises a data transfer means for outputting and receiving operating parameters and operating signals to and from the surgical instrument.

\* \* \* \* \*